(12) United States Patent
Frei et al.

(10) Patent No.: US 6,780,185 B2
(45) Date of Patent: Aug. 24, 2004

(54) OSTEOSYNTHETIC ANCHORING MEMBER

(75) Inventors: Reto Frei, Davos (CH); Markus Hehli, Frauenkirch (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 10/267,872

(22) Filed: Oct. 10, 2002

(65) Prior Publication Data

US 2003/0078581 A1 Apr. 24, 2003

Related U.S. Application Data

(63) Continuation of application No. PCT/CH00/00207, filed on Apr. 10, 2000.

(51) Int. Cl.[7] .............................................. A61B 17/74
(52) U.S. Cl. ........................................................ 606/68
(58) Field of Search ................................. 606/62–69, 72, 606/73; 411/340

(56) References Cited

U.S. PATENT DOCUMENTS

| | | | |
|---|---|---|---|
| 3,716,051 A | | 2/1973 | Fischer |
| 3,805,775 A | | 4/1974 | Fischer et al. |
| 4,236,512 A | | 12/1980 | Aginsky |
| 4,379,451 A | * | 4/1983 | Getscher ...................... 606/68 |
| 5,057,103 A | * | 10/1991 | Davis .......................... 606/63 |
| 5,458,599 A | * | 10/1995 | Adobbati ..................... 606/56 |
| 5,976,139 A | * | 11/1999 | Bramlet ....................... 606/66 |
| 6,224,600 B1 | * | 5/2001 | Protogirou .................. 606/63 |
| 6,299,630 B1 | * | 10/2001 | Yamamoto ................. 606/205 |
| 6,443,954 B1 | * | 9/2002 | Bramlet et al. .............. 606/62 |
| 6,500,177 B1 | | 12/2002 | Martinelli et al. ........... 606/57 |

FOREIGN PATENT DOCUMENTS

DE 19612276 10/1997

* cited by examiner

*Primary Examiner*—Michael J. Milano
*Assistant Examiner*—D. Jacob Davis
(74) *Attorney, Agent, or Firm*—Jones Day

(57) ABSTRACT

The invention relates to an osteosynthetic anchoring member comprising a longitudinal shaft extending along a longitudinal axis having a front shaft portion and a rear shaft portion, the front shaft portion insertable into a bone and comprising anchoring means for fixating the shaft in the bone and the rear shaft portion comprising anti-rotation means for permitting the rear shaft portion to be received in an implantable bone plate or a connecting member and to be secured against rotating about the longitudinal axis. The anchoring means are capable of being extended orthogonally with respect to the longitudinal axis of the shaft, and the rear shaft portion comprises tension means for extending the anchoring means to enable the anchoring member to be fixated within the bone. Also disclosed is a fixation device including such an anchoring member for fixating fractured femoral heads comprising the anchoring member to be fixated within the fractured femoral head, a plate to be screwed to the main part of the femur including a sleeve in which the anchoring member may be received and wherein it is displaceable coaxially to the longitudinal axis, and a compression bone screw to be screwed into the internal screw thread of a spindle.

43 Claims, 3 Drawing Sheets

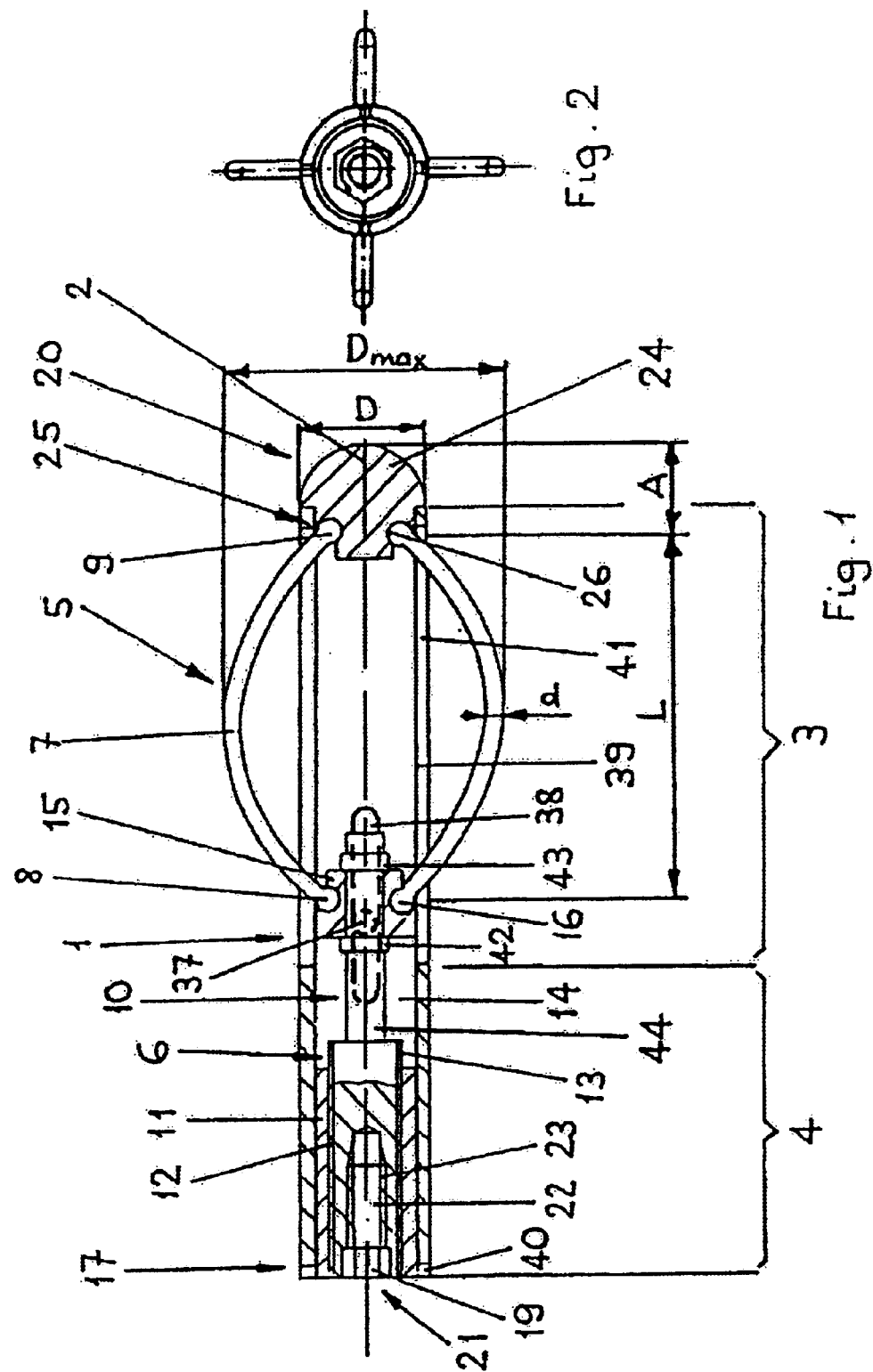

Section I-I

US 6,780,185 B2

OSTEOSYNTHETIC ANCHORING MEMBER

CROSS-REFERENCE TO RELATED APPLICATION

This application is a continuation of the U.S. National Stage designation of copending International Patent Application PCT/CH00/00207, filed Apr. 10, 2000. The entire content of this application is expressly incorporated herein by reference thereto.

FIELD OF THE INVENTION

The invention relates generally to an osteosynthetic anchoring member, and in particular to a fixation device for fixating fractured femoral heads including such an anchoring member.

BACKGROUND OF INVENTION

In the osteosynthetic treatment of fractures of the femoral neck, i.e. fractures of the femur in which the femoral neck linking the condyle with the rest of the femur is broken off, the bone fragments are generally temporarily linked together by means of a fixation device. One type of fixation device used for this type of fixation includes a) an anchor bolt to be screwed into a fractured condyle which has a headless shaft and an internal screw thread on its rear end; b) a plate to be screwed to the main part of the femur with a sleeve for receiving the shaft of the anchor bolt, and c) a compression bone screw to be screwed into the internal screw thread formed on the rear end of the anchor bolt, the head of which is supported by the rear shoulder surface of the sleeve. One example of such a device is shown in Switzerland Patent Application No. CH 634,742 to Sutter. A disadvantage of this type of anchor bolt resides in the fact that on screwing in the compression bone screw, a rotation of the anchor bolt must be avoided, as any turning of the anchor bolt would cause the anchor bolt to be driven further into the condyle instead of the desired effect of pressing the bone fragments against each other. For this reason, the anchor bolt in the sleeve must be prevented from rotation by means of a prismatic shape of the anchor bolt shaft and of the bore formed in the sleeve or by means of a key-and-slot connection between the anchor bolt and the sleeve. Thus, on implanting the fixation device, the surgeon is faced with the problem of having to place the plate with the sleeve in such a way over the anchor bolt that it engages exactly with the anti-rotation means. This difficulty is particularly aggravated by the fact that typically the anchor bolt does not protrude from the bone but is sunk into it by about 10 mm, which means that the surgeon cannot see the anchor bolt and has to spend much time trying to find the adequate position of the sleeve.

A need exists for an improved osteosynthetic anchoring member, and in particular for an osteosynthetic anchoring member which permits the sleeve to be placed in a simple manner over the anchoring member after the latter has been inserted into the bone, and which comprises an anti-rotation means arranged between the sleeve and the anchoring member to avoid a rotation of the femoral head, and which in addition optimally absorbs the occurring physiological strains. It is also desirable that the anchoring member allow an optimization of the strain absorption without necessitating a greater dimensioning of the anchoring member.

SUMMARY OF INVENTION

The present invention relates to an osteosynthetic anchoring member comprising a longitudinal shaft extending along a longitudinal axis having a front shaft portion and a rear shaft portion, the front shaft portion insertable into a bone and comprising anchoring means for fixating the shaft in the bone and the rear shaft portion comprising anti-rotation means for permitting the rear shaft portion to be received in an implantable bone plate or a connecting member and to be secured against rotating about the longitudinal axis. The anchoring means are capable of being extended orthogonally with respect to the longitudinal axis of the shaft, and the rear shaft portion comprises tension means for extending the anchoring means to enable the anchoring member to be fixated within the bone.

In one embodiment, the osteosynthetic anchoring member according to the invention comprises a prismatic or cylindrical shaft with a diameter D, a resilient anchoring means situated within said shaft and capable of bending outward radially relative to said shaft, and tension means located on the rear end of said shaft by means of which the anchoring means may be reversibly bent outward so as to enable the anchoring member to be anchored within the bone. The anchoring member has a longitudinal axis, a front end insertable into a bone, and a rear end insertable into an internal plate or a connecting member. By means of the tension means, the anchoring means may be bent outward in an arch-shaped manner so as to achieve a diameter Dmax>D. The ratio Dmax:D may be between 1.2 and 3, preferably between 1.5 and 2.5. The outward bending of the anchoring means advantageously takes place over a length L, which is between 10 and 60 mm. Preferably, the anchoring means may be bent outward elastically. In other embodiments, however, the anchoring means may also be subject to plastic deformation.

In one embodiment of the osteosynthetic anchoring member according to the invention, the anchoring means are shaped in the form of anchoring wires with a diameter d, each of which having a rear end adjacent or facing the tension means and a front end located opposite with respect to the longitudinal direction of the shaft. Preferably, in one embodiment, the anchoring member is equipped with between 3 and 6 anchoring wires.

The anchoring wires may be arranged parallel to the longitudinal axis, both ends thereof being located within the shaft and the anchoring wires being apt to be bent outward vertically to the longitudinal axis in an arch-shaped manner as the tension means is actuated. The diameter d of the anchoring wires is preferably between 0.5 mm and 2.5 mm, preferably between 1 mm and 1.5 mm. Advantageously, the ends of the anchoring wires are preferably spherical or ball shaped, the diameter of the balls being preferably greater than the diameter d. In another embodiment of the osteosynthetic anchoring member, the tension means is shaped in the form of a spindle which is arranged coaxially to the longitudinal axis of the shaft and the external screw thread of which may be screwed into a corresponding internal screw thread of a threaded sleeve which is located within a bore formed in the shaft in such a way as to extend concentrically to the longitudinal axis and to be secured against axial displacement and rotation. The spindle comprises a bearing member with an annular groove located towards the front shaft portion and displaceable within the bore parallel to the longitudinal axis. The annular groove is arranged on the bearing member in a cross-section vertical to the longitudinal axis and serves for receiving the rear ends of the anchoring wires. The bearing member is connected to the spindle in such a way that it is secured against axial displacement but capable of rotating about the longitudinal axis. In the lateral area of the bore formed in the shaft, a groove is arranged which extends parallel to the longitudinal axis and engages with a finger projecting radially from the bearing member. The configuration of the groove in the bore of the shaft and of the finger on the bearing member allows said bearing member to be axially displaced by the spindle while being secured against rotation relative to the shaft. Thus, it can be avoided that the turning of the spindle results in a torque exerted on the anchoring wires. For the purpose of rotating the spindle, means for receiving a screw driver, such as a hexagon socket or a groove, may be provided on the rear end thereof. In addition, the spindle may be provided on its rear end with a coaxial bore including an internal screw thread for receiving a compression bone screw.

In another embodiment, a plug member is positioned on the front end of the shaft and partially inserted into the bore and which may be convex, preferably spherical on the side opposite to the front shaft end, the convex part of the plug member forming the front end portion of the anchoring member. On its portion projecting into the bore, the plug member may in turn be provided with an annular groove, extending in a plane vertical to the longitudinal axis, which serves for receiving the front ends of the anchoring wires. Advantageously, both annular grooves have a circular cross-section. The rear shaft end may be provided with means for receiving a screw driver, shaped for example in the form of a groove. With the aid of a screw driver blocking said groove, the shaft may thus be secured against rotating together with the spindle, as the spindle is turned.

The invention also relates to a fixation device that serves for fixating fractured femoral heads and comprises in addition to the anchoring member according to the invention, which is fixed within the spongiosa of the fractured condyle by an outward bending of the anchoring wires, a plate to be screwed against the main part of the femur including a sleeve in which the part of the anchoring member adjoining its rear end may be received and wherein said anchoring member is displaceable coaxially to the longitudinal axis, and a compression bone screw to be screwed into the internal screw thread formed in the spindle on the rear shaft end, the head of which is supported by a shoulder surface of the sleeve. By rotating this compression bone screw, the fractured femoral head may be pulled close to the neck of the femur. An anti-rotation means is provided between the anchoring member and the sleeve, preventing a rotation of the femoral head about the longitudinal axis of the anchoring member.

Advantageously the aptitude of bending outward radially of the anchoring means of the osteosynthetic anchoring member allows the anchoring member to be anchored within a great volume of the bone. This may be of particular advantage in cases of osteoporotic bone. In addition, the plate with the sleeve may easily be placed over the anchoring member of the present invention, once said anchoring member has been anchored in the bone, which greatly facilitates the implantation of the entire fixation device.

BRIEF DESCRIPTION OF THE DRAWINGS

Preferred features of the present invention are disclosed in the accompanying drawings, wherein similar reference characters denote similar elements throughout the several views, and wherein:

FIG. 1 is a view of one preferred embodiment of the osteosynthetic anchoring member according to the invention;

FIG. 2 is a view of the embodiment of the osteosynthetic anchoring member shown in FIG. 1 as seen from the side of the plate;

DETAILED DESCRIPTION OF THE PREFERRED EMBODIMENTS

Figure 3:
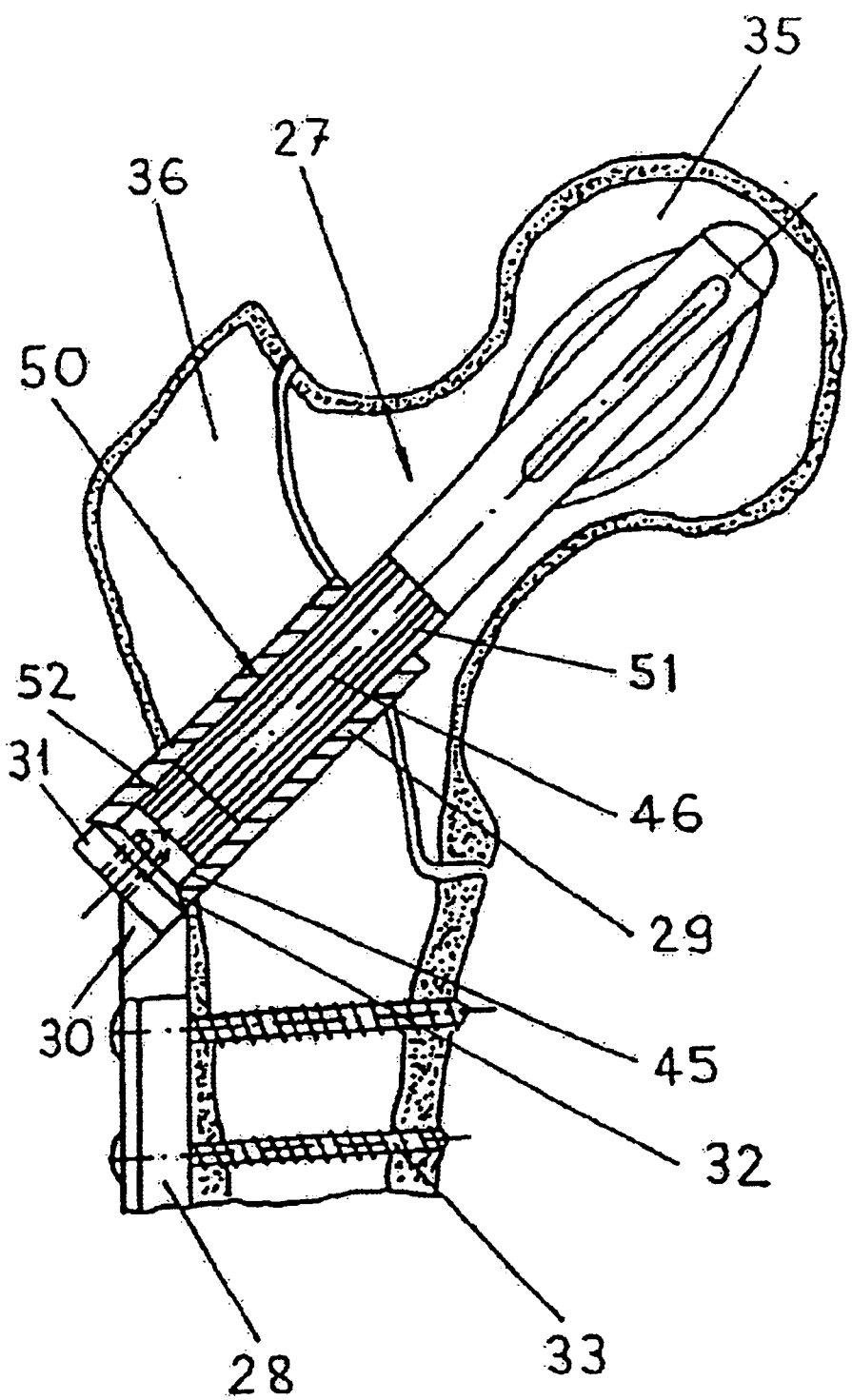
FIG. 3 shows a longitudinal section of an anchoring member according to one embodiment of the invention implanted in the femur as part of an embodiment of a fixation device for fixating a fractured femoral head.

FIGS. 1 and 2 show one embodiment of the osteosynthetic anchoring member according to the invention including a cylindrical shaft 1 with a diameter D extending along a longitudinal axis 2. Shaft 1 includes a front shaft portion 3 insertable into the bone and a rear shaft portion 4 insertable into an internal plate 28 or into another connecting member. Shaft 1 has a bore 14 extending concentrically therethrough forming a tube the wall of which is provided on the front shaft portion 3 with slots 41 extending parallel to the longitudinal axis and radially penetrating the wall of the tube. Through these slots 41, anchoring wires 7 may be passed which are able to be resiliently bent radially outward in an arch-shaped manner. The anchoring wires 7 may be bent outward, or inversely be moved back to their initial position, through these slots 41 by means of tension means 6 provided within the shaft 1. These anchoring wires 7 have a diameter d, a front end 9 and a rear end 8, as considered in a direction parallel to the longitudinal axis. These ends 8;9 are spherical, the diameter of the balls being greater than the diameter d. On the front end 20 of shaft 1, a plug member 24 is partially inserted into the bore 14, the part of the plug member projecting coaxially over the shaft 1 being shaped in a spherical form and forming the front end portion of the anchoring member. On the cylindrical portion 25 of the plug member 24 projecting into the bore 14, an annular groove 26 is provided which extends in a plane vertical to the longitudinal axis 2. This annular groove 26 has a circular cross-section and serves for receiving the front ends 9 of the anchoring wires 7.

The tension means 6 is shaped in the form of a spindle 10 accommodated coaxially to the longitudinal axis 2 within the shaft 1, the external screw thread 13 of which may be screwed into a corresponding internal screw thread 12 of a threaded sleeve 11. In the rear shaft portion 4, the screwed sleeve 11 is located in the bore 14 extending concentrically to the longitudinal axis 2 within the shaft 1 in such a way as to be secured against axial displacement and rotation. The spindle 10 comprises a bearing member 15 with an annular groove 16 located towards the front shaft portion 3 and displaceable within the bore 14 parallel to the longitudinal axis 2, said annular groove being arranged on the bearing member 15 in a plane vertical to the longitudinal axis 2 and serving for receiving the rear ends 8 of the anchoring wires 7. The bearing member 15 is provided with a coaxial bore and is rotatably mounted on a cylindrical portion 44 of the spindle 10 forming a coaxial prolongation of the external screw thread 13 of the spindle 10 on the side directed towards the front shaft portion 3. By means of a ring 42 on the side facing the external screw thread 13 of the spindle 10, and by means of a circlip 43 on the side facing the front shaft portion 3, the bearing member 15 is mounted on the spindle 10 in such a way as to be secured against axial displacement while being rotatable about the longitudinal axis 2. Instead of the circlip 43 a nut may be used for fixing the bearing member 15 on the spindle 10, said nut being apt to be screwed on a corresponding external screw thread formed in the cylindrical portion 44 of the spindle 10. In order to prevent the bearing member 15 from getting jammed between the nut and the ring 42 as the nut is tightened, a shoulder may be formed on the cylindrical portion 44 between the ring 42 and the external screw thread which serves as a stop for the nut. In the lateral area 39 of the bore 14 formed in the shaft 1, a groove 38 is arranged which extends parallel to the longitudinal axis 2 and engages with a finger 37 projecting radially from the bearing member 15. The configuration of the groove 38 in the bore 14 of the shaft 1 and of the finger 37 on the bearing member 15 allows said bearing member 15 to be axially displaced by the spindle 10 while being secured against rotation relative to the shaft 1. For the purpose of rotating the spindle 10, a hexagon socket 19 for receiving a corresponding screw driver is provided on its rear end 18. In addition, the spindle 10 is provided on its rear end 18 with a coaxial bore 22 equipped with an internal screw thread 23 the outside diameter of which is smaller than that of the hexagon socket 19 and which serves for receiving a compression bone screw (FIG. 3). The rear shaft end 17 is provided with a slot 40 which serves for receiving a corresponding screw driver.

FIG. 3 illustrates one use of the anchoring member according to the invention as part of a fixation device for fixating a fractured femoral head 35 on the femur 36. The anchoring member is anchored in the spongiosa of the femoral head 35 by means of the anchoring wires 7 which are bent outward as the spindle 10 is screwed into the screwed sleeve 11. The internal plate 28 fixed to the main part of the femur 36 by means of bone screws 33 is provided with a sleeve 29 extending at an angle with the plate 28 and projecting into the bone, the shaft 1 of the anchoring member being mounted in the bore 45 of said sleeve in such a way as to be displaceable parallel to the longitudinal axis 46 of the bore 45. By means of a compression bone screw 30 which may be screwed into the internal screw thread 23 (FIG. 1) formed in the spindle 10 and the head 31 of which is supported by a corresponding shoulder surface 32 formed on the end portion of the sleeve 29 facing the plate, the anchoring member may be fixed in such a way that tensile forces may be applied on the anchoring member from the femoral head 35, while compressive forces exerted equally from the femoral head 35 result in an axial displacement of the anchoring member. The shortening which the fractured bone may possibly undergo during the healing process can effectively be absorbed by the capacity of the anchoring member of being displaced within the sleeve 29. If the anchoring member did not accommodate to this shortening, there would in fact be a risk for the shaft 1 to penetrate the femoral head 35. Furthermore, an anti-rotation means 50 is provided between the anchoring member 27 and the sleeve 29 which prevents the femoral head 35 from rotating about the longitudinal axis 2. In this embodiment of the fixation device according to the invention, the anti-rotation means 50 comprises an external toothing 51 formed on the rear shaft portion 4 and a complementary internal toothing 52 formed in the bore 45 of the sleeve 29.

Figure 4:
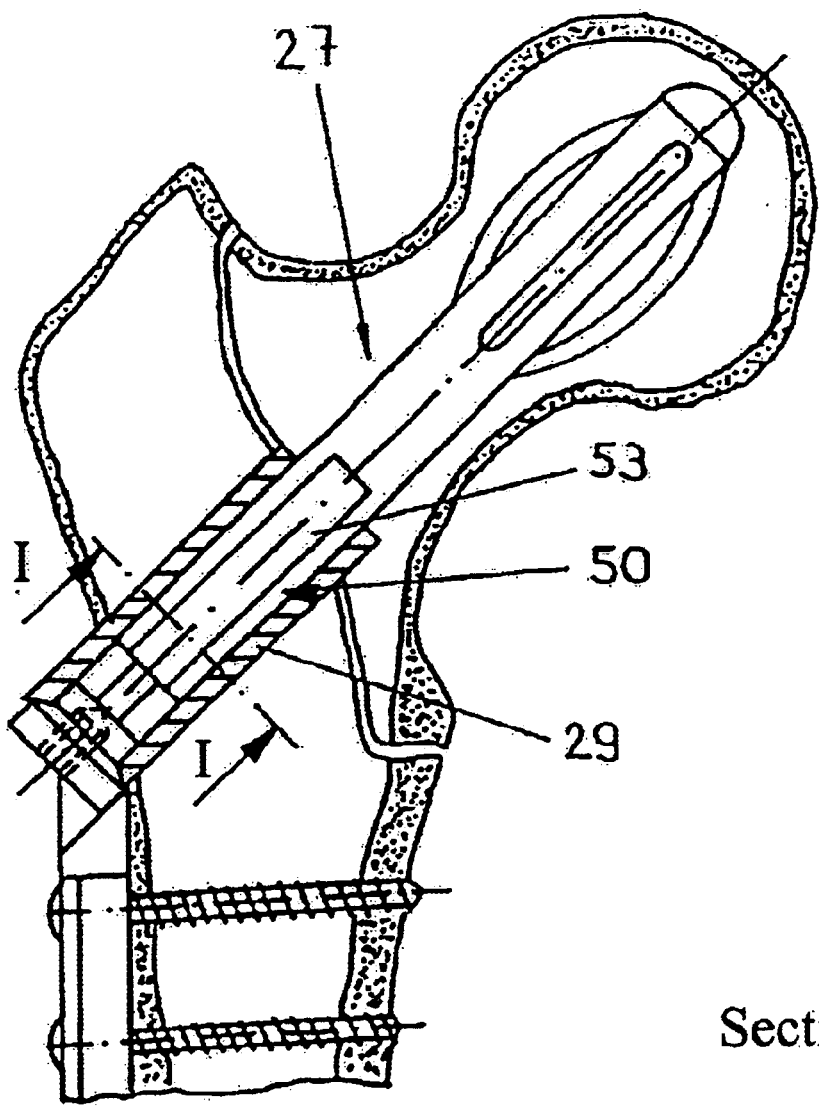
FIG. 4 shows a longitudinal section of an anchoring member according one embodiment of the invention implanted in the femur as part of another embodiment of a fixation device for fixating a fractured femoral head.
Figure 5:
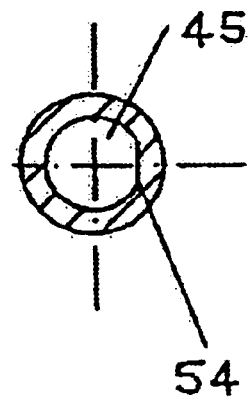
FIG. 5 is a cross-sectional view of the embodiment of the fixation device shown in FIG. 4.

FIGS. 4 and 5 show an embodiment of the fixation device according to the invention which differs from the embodiment shown in FIG. 3 only in so far as the anti-rotation means 50 provided between the anchoring member 27 and the sleeve 29 comprises a radially recessed flat 53 formed in the rear shaft portion 4 and a complementary projection 54 formed in the bore 45 of the sleeve 29 so that a cut-out in the shape of a segment of a circle is obtained in the circular cross-section of the bore 45, the central angle of said segment of a circle being 60 degrees. Instead of the embodiments of the anti-rotation means 50 shown in FIGS. 3, 4, and 5, the anti-rotation means 50 may also be realized in the form of a groove combined with a complementary cam. A detailed description of the surgical technique used for implanting such fixation devices is given in the publications CH 634,741 and CH 634,742.

One of ordinary skill in the art can envision numerous variations and modifications to the invention disclosed herein. All of these modifications are contemplated by the true spirit and scope of the following claims.

What is claimed is:

1. An osteosynthetic anchoring member for fixating bones, comprising:
    a longitudinal shaft extending along a longitudinal axis; the shaft including at least one slot and a front shaft portion and a rear shaft portion, the front shaft portion being insertable into a bone and comprising anchoring means for fixating the shaft in the bone and the rear shaft portion comprising anti-rotation means for permitting the rear shaft portion to be received in an implantable bone plate or a connecting member and to be secured against rotating about the longitudinal axis, wherein
        A) the anchoring means includes at least one anchoring wire aligned with the at least one slot for extending therethrough, and
        B) the rear shaft portion comprises tension means for contracting and extending the anchoring means to enable the anchoring member to be fixated within the bone,
    wherein the at least one anchoring wire has a front end and a rear end, the front end secured by the shaft while the rear end is sized and configured to engage the tension means.

2. The anchoring member of claim 1, wherein the anchoring means is configured and dimensioned to be bendable outward in an arch-shaped manner parallel to the longitudinal axis.

3. The anchoring member of claim 1, wherein the shaft is cylindrical and has a diameter D.

4. The anchoring member of claim 3, wherein the anchoring means is configured and dimensioned to be bendable outward to define a diameter Dmax, wherein diameter Dmax is greater than diameter D.

5. The anchoring member of claim 1, wherein the anchoring means are resiliently bendable in the radial outward direction.

6. The anchoring member of claim 1, wherein the anchoring means are plastic deformably bendable in the radial outward direction.

7. The anchoring member of claim 4, wherein the ratio of diameter Dmax to diameter D is between 1.2 and 3.0.

8. The anchoring member of claim 7, wherein the ratio of diameter Dmax to diameter D is between 1.5 and 2.5.

9. The anchoring member of claim 1, wherein the anchoring means is bendable outwardly over a length L and the length L is between 10 mm and 60 mm.

10. The anchoring member of claim 1, wherein the at least one anchoring wire is arranged parallel to the longitudinal axis and has a diameter d, the front and rear ends being mounted within the shaft, and the at least one anchoring wires is bendable outward in an arch shaped manner orthogonal to the longitudinal axis when the tension means is actuated.

11. The anchoring member of claim 10, wherein the anchoring means comprises between three and six anchoring wires.

12. The anchoring member of claim 10, wherein the diameter d is between 0.5 mm and 2.5 mm.

13. The anchoring member of claim 12, wherein the diameter d is between 1 mm and 1.5 mm.

14. The anchoring member of claim 10, wherein the front and rear ends are ball-shaped, with the ball diameter approximately equal to d.

15. The anchoring member of claim 1, wherein the tension means comprises, in coaxial alignment with the longitudinal axis, a spindle with an external screw thread and a threaded sleeve with an internal screw thread corresponding to the external screw thread.

16. The anchoring member of claim 15, wherein the shaft comprises a bore extending concentrically to the longitudinal axis within which the threaded sleeve and the spindle are arranged coaxially in the rear shaft portion, and the threaded sleeve is in fixed engagement with the bore.

17. The anchoring member of claim 15, wherein
A) the spindle comprises a bearing member with an annular groove positioned adjacent the front shaft portion and displaceable within a bore parallel to the longitudinal axis,
B) the spindle is connected to the bearing member and secured against axial displacement while being capable of rotating about the longitudinal axis;
C) lateral area of the bore formed in the shaft comprises a groove extending parallel to the longitudinal axis;
D) the bearing member comprises a radially projecting finger which engages with the groove, and
E) the annular groove is arranged in a cross-section extending vertically to the longitudinal axis receives the rear ends of the anchoring wires.

18. The anchoring member of claim 17, wherein the annular groove has a circular cross-section.

19. The anchoring member of claim 15, wherein the rear shaft portion has a rear shaft end longitudinally opposite to the front shaft portion, and the spindle has a rear spindle end which corresponds to the rear shaft end and comprises means for receiving a screw driver.

20. The anchoring member of claim 15, wherein the rear shaft portion has a rear shaft end longitudinally opposite to the front shaft portion, and the spindle has a rear spindle end which corresponds to the rear shaft end and comprises a bore extending from the rear spindle end concentrically to the longitudinal axis and including an internal screw thread for receiving a compression bone screw.

21. The anchoring member of claim 1, wherein the front shaft portion has a front shaft end longitudinally opposite to the rear shaft portion and the front shaft end comprises a plug member which is inserted into a bore and has a spherically shaped portion adjacent the front shaft end.

22. The anchoring member of claim 21, wherein the plug member includes an insertion portion to be inserted into the bore and the insertion portion comprises an annular groove, the annular groove arranged generally perpendicular to the longitudinal axis and for receiving the front ends of the anchoring wires.

23. The anchoring member of claim 22, wherein the annular groove has a circular cross-section.

24. The anchoring member of claim 1, wherein the shaft has a prismatic shape.

25. The anchoring member of claim 1, wherein the rear shaft end includes means for receiving a screw driver.

26. A fixation device for fixating fractured femoral heads including an anchoring member according to claim 1, wherein the fixation device comprises:
A) the anchoring member to be fixed within a fractured femoral head;
B) a plate positioned adjacent the main part of the femur and including a sleeve extending at an angle with respect to the plate in which the rear shaft portion of the anchoring member may be received and wherein it is displaceable coaxially to the longitudinal axis;
C) a compression bone screw to be screwed into the internal screw thread of a spindle, the head of which is supported by the shoulder surface of the sleeve; and
D) an anti-rotation means located between the anchoring member and the sleeve.

27. The fixation device of claim 26, wherein the fixation device further comprises bone screws for fixating the plate to the femur.

28. An anchoring member for bone fixation comprising:
a shaft disposed along a longitudinal axis with a bore extending therein along the axis and a slot extending from an outer surface of the shaft to the bore;
an anchoring wire having a first end and a second end, the wire being aligned with the slot for extending therethrough; and
a tensioning mechanism moveable within the bore and operatively associated with the second end of the anchoring wire;
wherein movement of the first end of the anchoring wire is fixed with respect to the shaft.

29. The anchoring member of claim 28, further comprising a plug member disposed proximate an end of the shaft, wherein movement of the first end of the anchoring wire is constrained by the plug member.

30. The anchoring member of claim 29, wherein the first end of the anchoring wire is received in a groove in the plug member.

31. The anchoring member of claim 29, wherein the plug member abuts an end of the shaft.

32. The anchoring member of claim 28, wherein the tension mechanism comprises a spindle.

33. The anchoring member of claim 32, wherein the spindle comprises a bearing portion and the second end of the anchoring wire is operatively associated with the bearing portion.

34. The anchoring member of claim 33, wherein the first and second ends of the anchoring wire each comprise an arcuate shape.

35. The anchoring member of claim 33, wherein the bearing portion comprises an arcuate groove, and the second end of the anchoring wire comprises an arcuate shape configured and dimensioned to be received in the arcuate groove.

36. The anchoring member of claim 28, wherein the tensioning mechanism is configured and dimensioned to permit movement thereof in the bore without rotation of the shaft.

37. The anchoring member of claim 28, further comprising:
a second slot extending from an outer surface of the shaft to the bore; and
a second anchoring wire aligned with the second slot for extending therethrough.

38. An anchoring member for bone fixation comprising:
a shaft disposed along a longitudinal axis with a bore extending therein along the axis and a plurality of slots extending from an outer surface of the shaft to the bore;

a plurality of anchoring wires each having a first end, a second end, and being aligned with one of the slots for extending therethrough; and a tensioning mechanism comprising a spindle moveable within the bore and operatively associated with the first end of each of the anchoring wires;

wherein the spindle is configured and dimensioned to permit movement thereof along the longitudinal axis without rotation of the shaft, and wherein movement of the second end of each of the anchoring wires is fixed with respect to the shaft.

39. The anchoring member of claim 38, wherein the distance between the first and second ends is adjustable.

40. The anchoring member of claim 38, wherein the first and second ends each comprise a spherical portion.

41. The anchoring member of claim 38, wherein the first end comprises a spherical portion and the spindle comprises a groove configured and dimensioned to receive the spherical portion.

42. An anchoring system for bone fixation comprising:

(1) an anchoring member comprising:

a shaft disposed along a longitudinal axis with a bore extending therein along the axis and a plurality of slots extending from an outer surface of the shaft to the bore;

a plurality of anchoring wires each aligned with one of the slots for extending therethrough; and a tensioning mechanism comprising a spindle moveable within the bore and operatively associated with a first end of each of the anchoring wires;

wherein the spindle is configured and dimensioned to permit movement thereof along the longitudinal axis without rotation of the shaft, and wherein movement of a second end of each of the anchoring wires is fixed with respect to the shaft;

(2) a plate; and (3) a bone screw for securing the plate to bone.

43. The anchoring system of claim 42, further comprising a sleeve extending from the plate, wherein the anchoring member is received in the sleeve.

* * * * *